United States Patent
Aoki et al.

(10) Patent No.: US 11,319,278 B2
(45) Date of Patent: May 3, 2022

(54) METHOD FOR PRODUCING GLYCINE

(71) Applicant: SHOWA DENKO K.K., Tokyo (JP)

(72) Inventors: Takanori Aoki, Setagaya-ku (JP); Akira Shibuya, Kawasaki (JP); Takamitsu Kobayashi, Fujisawa (JP); Hideo Miyata, Yokohama (JP); Shinya Tsukamoto, Kawasaki (JP); Manabu Kuwajima, Yokohama (JP); Motoki Murai, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 600 days.

(21) Appl. No.: 16/317,988

(22) PCT Filed: Jul. 11, 2017

(86) PCT No.: PCT/JP2017/025216
§ 371 (c)(1),
(2) Date: Jan. 15, 2019

(87) PCT Pub. No.: WO2018/021010
PCT Pub. Date: Feb. 1, 2018

(65) Prior Publication Data
US 2021/0292273 A1    Sep. 23, 2021

(30) Foreign Application Priority Data
Jul. 28, 2016    (JP) .............................. JP2016-148341

(51) Int. Cl.
C07C 227/26    (2006.01)
(52) U.S. Cl.
CPC ................................ C07C 227/26 (2013.01)

(58) Field of Classification Search
None
See application file for complete search history.

(56) References Cited

U.S. PATENT DOCUMENTS

2017/0275247 A1*    9/2017    Matsumura ............. C07B 61/00

FOREIGN PATENT DOCUMENTS

| | | | |
|---|---|---|---|
| CN | 103351306 A | | 10/2013 |
| JP | 54-46717 A | | 4/1979 |
| JP | 3-93757 A | | 4/1991 |
| JP | H0393757 | * | 4/1991 |
| JP | 2010-535182 A | | 11/2010 |
| WO | 2015/099053 A1 | | 7/2015 |
| WO | 2016/047516 A1 | | 3/2016 |

OTHER PUBLICATIONS

Masazumi Tamura, et al., "Efficient and Substrate-Specific Hydration of Nitriles to Amides in Water by Using a $CeO_2$ Catalyst", Chemistry A European Journal, 2011, pp. 11428-11431, vol. 17, No. 41.
International Search Report for PCT/JP2017/025216 dated Oct. 3, 2017 [PCT/ISA/210].

* cited by examiner

Primary Examiner — Amy C Bonaparte
(74) Attorney, Agent, or Firm — Sughrue Mion, PLLC

(57) ABSTRACT

Provided is a method for producing glycine, in which on synthesizing glycine from glycinonitrile, glycine can be obtained in a higher yield than that in the conventional method. The present invention relates to a method for producing glycine, including allowing glycinonitrile and water to react with each other in the presence of a cerium compound, optionally adding ammonia thereto, to obtain glycine.

4 Claims, No Drawings

METHOD FOR PRODUCING GLYCINE

CROSS REFERENCE TO RELATED APPLICATIONS

This application is a National Stage of International Application No. PCT/JP2017/025216, filed on Jul. 11, 2017, which claims priority from Japanese Patent Application No. 2016-148341, filed on Jul. 28, 2016.

TECHNICAL FIELD

The present invention relates to a method for producing glycine from glycinonitrile.

BACKGROUND ART

Glycine is one kind of amino acids constituting a basic unit of protein and is also referred to as aminoacetic acid, and glycine is widely used as an important fine chemical intermediate in the fields of agricultural chemicals, medicines, foods, livestock feeds, and so on.

As its production method, in addition to a method of hydrolyzing a natural protein, a chemical synthesis method, a fermentation method, and an enzymatic method are adopted. Among those, as the chemical synthesis method, so-called hydantoin method and Strecker method, and so on are widely known.

The hydantoin method is a method in which an aldehyde or ketone compound is allowed to react with hydrogen cyanide and ammonium carbonate to synthesize hydantoin, which is then subjected to alkaline hydrolysis to obtain glycine. In order to produce glycine by this method, after the alkaline hydrolysis, it is necessary to repeat a separation step of glycine crystallized through neutralization with an acid, and a desalting step for removing a salt formed through neutralization is also needed. Thus, there was such a problem that the number of steps becomes large in the hydantoin method.

Meanwhile, the Strecker method is a method in which an aldehyde or ketone compound is allowed to react with hydrogen cyanide and ammonia to synthesize glycinonitrile, which is then hydrolyzed to obtain glycine. In the Strecker method, conventionally, the hydrolysis of glycinonitrile was also executed with an alkali, and similar to the aforementioned hydantoin method, neutralization with an acid was needed, and a desalting step for removing the thus formed salt was needed.

As a method for simplifying such complicated steps, for example, PTL 1 proposes a method in which in the conventional Strecker method, glycinonitrile is hydrolyzed by bringing into contact with water in the presence of zirconium oxide and also in the co-existence of a ketone, thereby producing glycine.

CITATION LIST

Patent Literature

PTL 1: JP 3-93757 A

SUMMARY OF INVENTION

Technical Problem

In PTL 1, it is mentioned that since zirconium oxide exhibits high catalytic activity in the hydrolysis reaction of glycinonitrile, glycine can be obtained in a high yield without using an alkali or an acid in the reaction or the post-treatment, and that the yield can be further improved by allowing zirconium oxide and a ketone to coexist.

However, actually, even in the case of using only zirconium oxide as the catalyst, or in the case of further allowing a ketone to coexist therein, it is hardly said that the yield of glycine is industrially satisfactory.

In consequence, as the catalyst to be used for producing glycine through hydrolysis of glycinonitrile, one with which glycine is obtained in a higher yield has been demanded.

Under the foregoing circumstances, the present invention has been made, and an object thereof is to provide a method for producing glycine, in which on synthesizing glycine from glycinonitrile, glycine can be obtained in a higher yield than that in the conventional method.

Solution to Problem

The present invention is based on finding that in hydrolysis of glycinonitrile, a cerium compound exhibits a more excellent catalyst performance than zirconium oxide, and enables glycine to be obtained in a high yield.

Specifically, the present invention provides the following [1] to [6].

[1] A method for producing glycine, including allowing glycinonitrile and water to react with each other in the presence of a cerium compound, to obtain glycine.

[2] The method for producing glycine as set forth in above [1], wherein the cerium compound is a cerium-containing oxide.

[3] The method for producing glycine as set forth in above [2], wherein the cerium-containing oxide is a cerium oxide, or a complex metal oxide of cerium and at least one other metal element.

[4] The method for producing glycine as set forth in above [2], wherein the cerium-containing oxide is a supported type metal oxide in which a component containing at least one metal element selected from the group consisting of lithium, magnesium, iron, cobalt, nickel, copper, strontium, yttrium, zirconium, indium, barium, lanthanum, praseodymium, neodymium, europium, lead, hafnium, and zinc is supported on a cerium oxide or a complex metal oxide of cerium and at least one other metal element.

[5] The method for producing glycine as set forth in above [3] or [4], wherein the other metal element in the complex metal oxide contains zirconium.

[6] The method for producing glycine as set forth in any one of above [1] to [5], including adding ammonia into a reaction system where glycinonitrile and water are allowed to react with each other in the presence of the cerium compound.

Advantageous Effects of Invention

In accordance with the production method of the present invention, on synthesizing glycine from glycinonitrile, by using a catalyst having high activity and high selectivity in a catalytic reaction between glycinonitrile and water, the yield of glycine can be improved as compared with the conventional method.

In consequence, the production method of the present invention is a useful method for industrial production of glycine.

DESCRIPTION OF EMBODIMENTS

The present invention is hereunder described in detail.

The method for producing glycine of the present invention includes allowing glycinonitrile and water to react with each other in the presence of a cerium compound, to obtain glycine.

On synthesizing glycine from glycinonitrile, by using a cerium compound as a catalyst and performing a catalytic reaction with water in the presence of the catalyst, the hydrolysis reaction is selectively promoted, whereby glycine can be obtained in a higher yield than that in the case of using a conventional catalyst.

[Cerium Compound]

Examples of the cerium compound which is used as the catalyst include an oxide, a halide, an inorganic acid salt (for example, a sulfate, a nitrate, a carbonate, or a phosphate), an acetate, an oxalate, and a hydroxide, each of which contains cerium. Among those, a cerium-containing oxide represented by a cerium oxide is preferred because it is excellent in catalyst performance.

The cerium-containing oxide is preferably a cerium oxide or a complex metal oxide of cerium and at least one other metal element. That is, the metal element constituting the cerium-containing oxide may be either cerium alone or two or more metal elements including cerium. In addition, as the cerium-containing oxide, two or more cerium-containing oxides which are different in composition or physical properties, such as shape and particle diameter, may be used in combination.

Examples of the cerium oxide include cerium(II) oxide ($Ce_2O_3$), cerium(IV) oxide ($CeO_2$), and a mixture thereof or a cerium oxide compound having a mixed phase thereof. Among those, cerium(IV) oxide ($CeO_2$) is preferred.

(Complex Metal Oxide)

Though the metal element other than cerium in the complex metal oxide is not particularly limited, examples thereof include lithium, magnesium, iron, cobalt, nickel, copper, strontium, yttrium, zirconium, indium, barium, lanthanum, praseodymium, neodymium, europium, lead, hafnium, and zinc. These may be used either alone or in combination of two or more thereof. Among those, zirconium, yttrium, and lanthanum are preferred, and it is more preferred to contain zirconium.

As the complex metal oxide, a cerium zirconium complex oxide, such as $CeZrO_4$ ($CeO_2$—$ZrO_2$), is preferred. It is to be noted that the complex metal oxide may be an oxide solid solution containing cerium.

Based on all of the metals including cerium contained in the complex metal oxide, the content of cerium is preferably 5 mol % or more and less than 100 mol %, more preferably 30 to 99 mol %, and still more preferably 45 to 95 mol %.

Though the production method of a complex metal oxide is not particularly limited, the complex metal oxide can be, for example, produced by adopting a hydrothermal synthesis method, a coprecipitation method, or a sol-gel method. Specifically, examples thereof include a method in which two or more precursors containing a cerium compound are mixed in a solvent and heated; and a method in which a precursor containing a cerium compound is baked in an atmosphere of an oxidative gas, such as air.

Examples of the precursor of the cerium compound include a salt, such as an acetate, a nitrate, a sulfate, a carbonate, and an organic acid salt; a halide, such as a chloride, a bromide, and an iodide; a hydroxide; an alkoxide; and an oxyhalide, each of which contains cerium. The precursor may be either an anhydride or a hydrate.

Examples of the solvent include polar solvents, such as water; an alcohol, e.g., methanol, ethanol, 1-propanol, 2-propanol, and 1-butanol; and a ketone, e.g., acetone. These may be used either alone or in combination of two or more thereof.

It is to be noted that the complex metal oxide, such as cerium zirconium complex oxide ($CeZrO_4$), is also available as a marketed product, and the marketed product can be used, too.

As for the complex metal oxide, from the viewpoint of improving the catalyst performance, those obtained through a heat treatment in an atmosphere of an oxidative gas, such as air; an inert gas, such as a nitrogen gas and an argon gas; a carbon dioxide gas, or the like may be used. Though the treatment temperature is not particularly limited, it is preferably 200 to 900° C., more preferably 300 to 850° C., and still more preferably 400 to 800° C.

The cerium compound may be used upon being mixed with a catalyst other than the cerium compound. Though such a catalyst is not particularly limited, examples thereof include an oxide, such as zirconium oxide, magnesium oxide, zinc oxide, and titanium oxide; and a clay mineral, such as hydrotalcite. Among those, zirconium oxide is preferred. Alternatively, an embodiment in which the cerium-containing oxide is supported on a carrier may be adopted for the catalyst.

(Supported Type Metal Oxide)

The cerium-containing oxide may be a supported type metal oxide in which a component containing at least one metal element selected from the group consisting of lithium, magnesium, iron, cobalt, nickel, copper, strontium, yttrium, zirconium, indium, barium, lanthanum, praseodymium, neodymium, europium, lead, hafnium, and zinc is supported on the cerium oxide or the complex metal oxide.

The metal element to be contained in the supporting component may be used alone or in combination of two or more thereof. Among those, lithium, lanthanum, neodymium, yttrium, europium, barium, and magnesium are preferred, and lithium is especially preferred.

From the viewpoint of improving the productivity of glycine, the amount of the metal element to be contained in the supporting component is preferably 0.01 to 10 parts by mass, more preferably 0.02 to 7.0 parts by mass, and still more preferably 0.05 to 5.0 parts by mass based on 100 parts by mass of cerium.

The production method of the supported type metal oxide is not particularly limited, and a known preparation method of supported catalyst can be adopted. Examples thereof include an impregnation method, a CVD method, and a spray drying method. In the case of an impregnation method, specifically, the supported type metal oxide can be suitably produced by the method described in the section of Examples as mentioned later.

A form of the cerium compound is not particularly limited, and examples thereof include a powder. In addition, from the viewpoint of handling, a material having been subjected to molding processing into a pellet form can be exemplified. This molding processing can be, for example, performed by adding a solvent, such as water, to a powdered cerium compound or a powder of a cerium compound supported on a carrier, to form a paste, which is then subjected to extrusion molding and baking.

(Glycinonitrile)

Though the production method of glycinonitrile, which is a reaction raw material of the present invention, is not particularly limited, in general, the glycinonitrile is obtained by allowing ammonia to react with glycolonitrile which is obtained through a reaction between formaldehyde and hydrogen cyanide. In the present invention, the thus obtained glycinonitrile may be purified and then used as the reaction raw material. Alternatively, the reaction solution per se can be provided for the production of glycine.

(Reaction)

The water to be used for the reaction between glycinonitrile and water is not only needed for the hydrolysis reaction of glycinonitrile but also can play a role as the reaction solvent. From such a viewpoint, the amount of water is preferably 0.5 to 100 times by mass, more preferably 1 to 50 times by mass, and still more preferably 1.5 to 20 times by mass relative to the glycinonitrile.

As for the reaction solvent, though water is preferably used, a solvent other than water may also be mixed and used. As for the solvent to be mixed with water, a solvent which is miscible with water, such as methanol, ethanol, 1-propanol, 2-propanol, 1,4-dioxane, tetrahydrofuran, N-methylpyrrolidinone, N-ethylpyrrolidinone, 1,3-dimethyl-2-imidazolidinone, dimethyl sulfoxide, and acetone, can be used.

In the reaction system between glycinonitrile and water, ammonia may be added. In the reaction in the presence of a cerium compound, by adding ammonia, the selectivity from glycinonitrile to glycine can be improved.

The addition method of ammonia is not particularly limited, and ammonia may be fed as a gas into the reaction solvent. Alternatively, ammonia may be mixed as an aqueous solution with the reaction solvent.

The concentration of ammonia added is preferably 1 to 30% by mass, more preferably 2 to 20% by mass, and still more preferably 5 to 15% by mass in the reaction solution having glycinonitrile dissolved therein.

The reaction mode may be either a batchwise mode or a continuous mode. As for the continuous mode, there is a continuous stirred-tank reactor (CSTR) mode and a plug flow reactor (PFR) mode, and either of these modes is adaptable.

In the case of a batchwise mode, the concentration of glycinonitrile charged in the reaction solution is preferably 1 to 66% by mass from the viewpoint of improving the productivity. In the case of not adding ammonia, the concentration of glycinonitrile charged is more preferably 1.5 to 50% by mass, still more preferably 2 to 40% by mass, and especially preferably 3 to 15% by mass. In the case of adding ammonia, the concentration of glycinonitrile charged is more preferably 2 to 20% by mass, and still more preferably 3 to 15% by mass.

Though the amount of the cerium compound used is properly set according to the reaction mode or the kind of the cerium compound, for example, in the case of a batchwise mode, it is preferably 1 to 300 parts by mass, more preferably 5 to 200 parts by mass, and still more preferably 10 to 150 parts by mass based on 100 parts by mass of glycinonitrile.

It is to be noted that in the case of a continuous mode, the concentration of glycinonitrile charged and the amount of the cerium compound used in the reaction solution can be properly set taking into consideration the number of reaction tanks or the stirring conditions, or the like in reference to the reactivity in the case of a batchwise mode.

The temperature on allowing glycinonitrile and water to react with each other is preferably 30 to 250° C., more preferably 40 to 200° C., and still more preferably 50 to 100° C. from the viewpoint of improving the yield of glycine.

The pressure at the time of the reaction is not particularly limited, and the reaction may be performed under autogenic pressure or may be performed under elevated pressure. In that case, the pressure is preferably 0.11 to 2.0 MPa, more preferably 0.15 to 1.0 MPa, and still more preferably 0.20 to 0.5 MPa in terms of an absolute pressure.

The time required for the aforementioned reaction is properly regulated according to the reaction mode or reaction temperature, the concentration of the raw material, the kind and the use amount of the cerium compound that is the catalyst, and so on. In the case where it is longer than necessary, even if the conversion of glycinonitrile is improved, other decomposition products but not the targeted glycine are liable to be produced, and thus, it is not preferred. From the viewpoint of improving the yield of glycine, the reaction time is preferably 0.2 to 20 hours, more preferably 0.5 to 18 hours, and still more preferably 0.7 to 15 hours.

It is to be noted that in the reaction between glycinonitrile and water, there is a case where glycine amide is produced by a hydration reaction without causing the production of glycine by the hydrolysis reaction. The thus produced glycine amide can be utilized as a raw material for producing glycine by being recovered, and then used as it is or mixed with glycinonitrile, which is the reaction raw material.

After completion of the reaction, the recovery method of glycine from the reaction solution is not particularly limited. Glycine can be, for example, obtained by separating the reaction solution from the catalyst through filtration, followed by concentration and crystallization. Furthermore, by performing recrystallization, the purity of glycine can be increased.

In accordance with the production method of the present invention, there is an advantage that glycine can be produced without producing a salt as an impurity at the time of the reaction, and without the need of a desalting step with an alkali or an acid in the post-treatment of the reaction.

The catalyst, the activity of which has been lowered due to the use for the reaction, may be reused. As for the reuse method, washing or a heat treatment can be performed. The washing can be, for example, performed by using water, an acid, an alkali, an organic solvent, etc. The heat treatment is preferably performed by heating at preferably 200 to 800° C., and more preferably 300 to 600° C. in a gas atmosphere of an oxidative gas, such as air; an inert gas, such as a nitrogen gas and an argon gas; carbon dioxide; or the like. The washing and the heat treatment may be performed in combination.

EXAMPLES

The present invention is hereunder described more specifically by reference to Examples, but it should be construed that the present invention is by no means limited by these Examples.

[Analysis Method]

In the production of glycinonitrile, Examples, and Comparative Examples as mentioned below, the purity and conversion of glycinonitrile, and the yield and conversion of each of glycine and glycine amide were determined by means of quantitative analysis by high performance liquid chromatography (HPLC). Specifically, glycinonitrile, glycine, and glycine amide in the reaction solution were measured under the following analysis conditions, and the respective values were calculated by the absolute calibration curve method.

<Analysis Conditions>

Column: Shodex RSpak NN-814 (manufactured by Showa Denko K.K.)

Column size: 8.0 mm×250 mm

Column temperature: 40° C.

Eluting solution: 0.1 v/v % phosphoric acid aqueous solution containing 8 mM of $KH_2PO_4$ Flow rate of eluting solution: 1.0 mL/min Detector: UV (ultraviolet ray) 210 nm, RI (refractive index)

Standard samples:

Glycinonitrile sulfate (aminoacetonitrile sulfate, manufactured by Tokyo Chemical Industry Co., Ltd.)

Glycine amide hydrochloride (manufactured by Tokyo Chemical Industry Co., Ltd.)

Glycine (manufactured by Junsei Chemical Co., Ltd.)

[Production of Glycinonitrile]

In a one-liter four-necked reaction vessel equipped with a cooling jacket-provided dropping funnel and a pH controller, 330 g of formalin having a concentration of 40% by mass was charged. The liquid properties were regulated to a pH of 5.0 by using a sodium hydroxide aqueous solution having a concentration of 25% by mass. In this liquid, 178 g of hydrocyanic acid having a concentration of 70% by mass was dropped through the dropping funnel while holding the pH at 4.9 to 5.1. After completion of dropping, the resulting mixture was allowed to react with stirring for about 30 minutes.

In a one-liter stainless steel-made autoclave charged with 320 g of ammonia water having a concentration of 28% by mass, this reaction solution was added over about 2 hours by using a liquid delivery pump while holding at a temperature of 50° C. and a pressure of 0.5 MPaG or less. After completion of addition, the resulting mixture was allowed to react at 50° C. with stirring for 2 hours.

This reaction solution was cooled, and the contents obtained by opening the autoclave were put into a one-liter eggplant type flask and distilled under reduced pressure, thereby obtaining 173 g of glycinonitrile having a purity of 99.5%.

In the following Examples and Comparative Examples, this glycinonitrile was used as a raw material, and production of glycine was performed.

[Catalysts Used]

Cerium oxide ($CeO_2$): Reference catalyst of the Catalysis Society of Japan, JRC-CEO-2

Zirconium oxide ($ZrO_2$): Manufactured by Junsei Chemical Co., Ltd.

Cerium zirconium complex oxide ($CeZrO_4$): Manufactured by Aldrich

Lithium-supported cerium oxide (Li-supported $CeO_2$): Prepared in the following method <Preparation Method>

In a glove box in a nitrogen gas atmosphere, 0.81 g of a 1% by mass aqueous solution of lithium nitrate (manufactured by Kanto Chemical Co., Inc.) was uniformly mixed with 1.0 g of cerium oxide ($CeO_2$: reference catalyst of the Catalysis Society of Japan, JRC-CEO-2) charged in a 9-mL vial made of a Pyrex (a registered trademark) glass by using a spatula while dropping. The resulting mixture was charged in a heating type vacuum dryer and dried at 50° C. for 1 hour under reduced pressure conditions. A solid obtained by drying was transferred into a crucible and baked in air at 500° C. for 3 hours, thereby obtaining a lithium-supported cerium oxide (Li-supported $CeO_2$).

[Production of Glycine]

Example 1

In a 15-mL glass-made pressure vessel having a stirrer put thereinto, 0.5 g of $CeO_2$ (concentration in liquid: 5.0% by mass relative to the glycinonitrile aqueous solution; 45 parts by mass based on 100 parts by mass of glycinonitrile (raw material)) was charged. To this, 10.0 g of a glycinonitrile aqueous solution having a concentration of 11.0% by mass was added. The pressure vessel was then hermetically closed, and stirring was performed at 70° C. for 1 hour. After the pressure vessel was cooled to room temperature (25° C.), the reaction solution within the vessel was subjected to HPLC analysis.

Examples 2 to 7

The same reaction as in Example 1 was performed, except that the reaction conditions of Example 1 were changed to the conditions shown in the following Table 1, and each of the reaction solutions was subjected to HPLC analysis.

Example 8

In a 15-mL glass-made pressure vessel having a stirrer put thereinto, 0.5 g of $CeO_2$ (concentration in liquid: 5.0% by mass relative to the glycinonitrile aqueous solution; 45 parts by mass based on 100 parts by mass of glycinonitrile (raw material)) was charged. To this, a 28% ammonia aqueous solution was added such that a concentration of ammonia in liquid was 10.0% by mass. Subsequently, 10.0 g of a glycinonitrile aqueous solution having a concentration of 11.0% by mass was added. The pressure vessel was then hermetically closed, and stirring was performed at 70° C. for 1 hour. After the pressure vessel was cooled to room temperature (25° C.), the reaction solution within the vessel was subjected to HPLC analysis.

Examples 9 and 10

The same reaction as in Example 8 was performed, except that the reaction conditions of Example 8 were changed to the conditions shown in the following Table 1, and each of the reaction solutions was subjected to HPLC analysis.

Comparative Examples 1 to 5

The same reaction as in Example 1 was performed, except that $ZrO_2$ was used in place of $CeO_2$ of Example 1; and that the conditions shown in the following Table 1 were adopted for the other reaction conditions, and each of the reaction solutions was subjected to HPLC analysis.

Comparative Examples 6 and 7

The same reaction as in Example 8 was performed, except that $ZrO_2$ was used in place of $CeO_2$ of Example 8; and that the conditions shown in the following Table 1 were adopted for the other reaction conditions, and each of the reaction solutions was subjected to HPLC analysis.

Examples 11 to 16

The same reaction as in Example 1 was performed, except that $CeZrO_4$ was used in place of $CeO_2$ of Example 1; and that the conditions shown in the following Table 2 were adopted for the other reaction conditions, and each of the reaction solutions was subjected to HPLC analysis.

Examples 17 to 19

The same reaction as in Example 8 was performed, except that $CeZrO_4$ was used in place of $CeO_2$ of Example 8; and that the conditions shown in the following Table 2 were adopted for the other reaction conditions, and each of the reaction solutions was subjected to HPLC analysis.

Examples 20 and 21

The same reaction as in Example 1 was performed, except that Li-supported $CeO_2$ was used in place of $CeO_2$ of Example 1; and that the conditions shown in the following Table 2 were adopted for the other reaction conditions, and each of the reaction solutions was subjected to HPLC analysis.

Examples 22 to 24

The same reaction as in Example 8 was performed, except that Li-supported $CeO_2$ was used in place of $CeO_2$ of Example 8; and that the conditions shown in the following Table 2 were adopted for the other reaction conditions, and each of the reaction solutions was subjected to HPLC analysis.

The conversion of glycinonitrile, and the yield and conversion of each of glycine and glycine amide in each of the aforementioned Examples and Comparative Examples are collectively shown in the following Tables 1 and 2. It is to be noted that in the tables, the expression "0" for the yield means that the peak in the analysis by HPLC was less than the detection lower limit, and in this case, the selectivity was also expressed as "0".

TABLE 1

| | Catalyst | Addition of ammonia | Amount of catalyst [mass %] | Amount of catalyst [parts by mass] (vs. 100 parts by mass of raw material) | Reaction temperature [° C.] | Reaction time [hr] | Glycinonitrile Concentration of raw material [mass %] |
|---|---|---|---|---|---|---|---|
| Example 1 | $CeO_2$ | No | 5.0 | 45 | 70 | 1 | 11.0 |
| Example 2 | $CeO_2$ | No | 5.0 | 100 | 70 | 1 | 5.0 |
| Example 3 | $CeO_2$ | No | 5.0 | 45 | 70 | 3 | 11.0 |
| Example 4 | $CeO_2$ | No | 5.0 | 45 | 50 | 15 | 11.0 |
| Example 5 | $CeO_2$ | No | 5.0 | 45 | 100 | 1 | 11.0 |
| Example 6 | $CeO_2$ | No | 5.0 | 23 | 70 | 3 | 22.0 |
| Example 7 | $CeO_2$ | No | 10.0 | 91 | 70 | 1 | 11.0 |
| Example 8 | $CeO_2$ | Yes | 5.0 | 45 | 70 | 1 | 11.0 |
| Example 9 | $CeO_2$ | Yes | 5.0 | 45 | 100 | 1 | 11.0 |
| Example 10 | $CeO_2$ | Yes | 5.0 | 45 | 70 | 3 | 11.0 |
| Comparative Example 1 | $ZrO_2$ | No | 5.0 | 45 | 70 | 1 | 11.0 |
| Comparative Example 2 | $ZrO_2$ | No | 5.0 | 100 | 70 | 1 | 5.0 |
| Comparative Example 3 | $ZrO_2$ | No | 5.0 | 45 | 70 | 3 | 11.0 |
| Comparative Example 4 | $ZrO_2$ | No | 5.0 | 23 | 70 | 3 | 22.0 |
| Comparative Example 5 | $ZrO_2$ | No | 10.0 | 91 | 70 | 3 | 11.0 |
| Comparative Example 6 | $ZrO_2$ | Yes | 5.0 | 45 | 70 | 1 | 11.0 |
| Comparative Example 7 | $ZrO_2$ | Yes | 5.0 | 45 | 70 | 3 | 11.0 |

| | Glycinonitrile Conversion [%] | Glycine amide (1) Yield [%] | Glycine amide (1) Selectivity [%] | Glycine (2) Yield [%] | Glycine (2) Selectivity [%] | (1) + (2) Yield [%] | (1) + (2) Selectivity [%] |
|---|---|---|---|---|---|---|---|
| Example 1 | 98.6 | 19.2 | 19.5 | 72.3 | 73.3 | 91.5 | 92.8 |
| Example 2 | 99.4 | 6.1 | 6.1 | 87.6 | 88.1 | 93.7 | 94.3 |
| Example 3 | 100 | 4.2 | 4.2 | 88.1 | 88.1 | 92.3 | 92.3 |
| Example 4 | 100 | 1.7 | 1.7 | 91.6 | 91.6 | 93.3 | 93.3 |
| Example 5 | 100 | 9.9 | 9.9 | 62.7 | 62.7 | 72.6 | 72.6 |
| Example 6 | 100 | 6.8 | 6.8 | 67.4 | 67.4 | 74.2 | 74.2 |
| Example 7 | 100 | 3.0 | 3.0 | 87.1 | 87.1 | 90.1 | 90.1 |
| Example 8 | 99.0 | 14.8 | 14.9 | 77.7 | 78.5 | 92.5 | 93.4 |
| Example 9 | 100 | 3.0 | 3.0 | 74.8 | 74.8 | 77.8 | 77.8 |
| Example 10 | 100 | 8.6 | 8.6 | 86.0 | 86.0 | 94.6 | 94.6 |
| Comparative Example 1 | 18.6 | 1.2 | 6.5 | 0.1 | 0.5 | 1.3 | 7.0 |
| Comparative Example 2 | 16.2 | 0 | 0 | 0 | 0 | 0 | 0 |
| Comparative Example 3 | 36.8 | 1.4 | 3.8 | 0 | 0 | 1.4 | 3.8 |
| Comparative Example 4 | 30.7 | 2.6 | 8.5 | 0 | 0 | 2.6 | 8.5 |
| Comparative Example 5 | 40.5 | 1.4 | 3.5 | 0.3 | 0.7 | 1.7 | 4.2 |
| Comparative Example 6 | 12.8 | 3.7 | 28.9 | 0.2 | 1.6 | 3.9 | 30.5 |
| Comparative Example 7 | 20.9 | 10.8 | 51.7 | 1.1 | 5.3 | 11.9 | 56.9 |

TABLE 2

| | Catalyst | Addition of ammonia | Amount of catalyst [mass %] | [parts by mass] (vs. 100 parts by mass of raw material) | Reaction temperature [° C.] | Reaction time [hr] | Glycinonitrile Concentration of raw material [mass %] |
|---|---|---|---|---|---|---|---|
| Example 11 | CeZrO$_4$ | No | 5.0 | 45 | 70 | 1 | 11.0 |
| Example 12 | CeZrO$_4$ | No | 5.0 | 100 | 70 | 1 | 5.0 |
| Example 13 | CeZrO$_4$ | No | 5.0 | 45 | 70 | 3 | 11.0 |
| Example 14 | CeZrO$_4$ | No | 5.0 | 45 | 100 | 1 | 11.0 |
| Example 15 | CeZrO$_4$ | No | 5.0 | 23 | 70 | 3 | 22.0 |
| Example 16 | CeZrO$_4$ | No | 10.0 | 91 | 70 | 3 | 11.0 |
| Example 17 | CeZrO$_4$ | Yes | 5.0 | 45 | 70 | 1 | 11.0 |
| Example 18 | CeZrO$_4$ | Yes | 5.0 | 45 | 70 | 3 | 11.0 |
| Example 19 | CeZrO$_4$ | Yes | 5.0 | 45 | 100 | 1 | 11.0 |
| Example 20 | Li-supported CeO$_2$ | No | 5.0 | 45 | 70 | 1 | 11.0 |
| Example 21 | Li-supported CeO$_2$ | No | 5.0 | 45 | 100 | 1 | 11.0 |
| Example 22 | Li-supported CeO$_2$ | Yes | 5.0 | 45 | 70 | 1 | 11.0 |
| Example 23 | Li-supported CeO$_2$ | Yes | 5.0 | 45 | 100 | 1 | 11.0 |
| Example 24 | Li-supported CeO$_2$ | Yes | 5.0 | 45 | 70 | 3 | 11.0 |

| | Glycinonitrile Conversion [%] | Glycine amide (1) Yield [%] | Glycine amide (1) Selectivity [%] | Glycine (2) Yield [%] | Glycine (2) Selectivity [%] | (1) + (2) Yield [%] | (1) + (2) Selectivity [%] |
|---|---|---|---|---|---|---|---|
| Example 11 | 93.6 | 5.0 | 5.3 | 75.1 | 80.2 | 80.1 | 85.6 |
| Example 12 | 96.8 | 4.0 | 4.1 | 86.4 | 89.3 | 90.4 | 93.4 |
| Example 13 | 99.7 | 2.0 | 2.0 | 84.4 | 84.7 | 86.4 | 86.7 |
| Example 14 | 98.9 | 3.3 | 3.3 | 74.7 | 75.5 | 78.0 | 78.9 |
| Example 15 | 100 | 2.1 | 2.1 | 69.2 | 69.2 | 71.3 | 71.3 |
| Example 16 | 100 | 0 | 0 | 83.8 | 83.8 | 83.8 | 83.8 |
| Example 17 | 96.2 | 4.7 | 4.9 | 80.7 | 83.9 | 85.4 | 88.8 |
| Example 18 | 99.4 | 8.3 | 8.4 | 80.3 | 80.8 | 88.6 | 89.1 |
| Example 19 | 98.8 | 2.6 | 2.6 | 70.7 | 71.6 | 73.3 | 74.2 |
| Example 20 | 100 | 23.2 | 23.2 | 65.6 | 65.6 | 88.8 | 88.8 |
| Example 21 | 100 | 6.1 | 6.1 | 73.9 | 73.9 | 80.0 | 80.0 |
| Example 22 | 100 | 14.3 | 14.3 | 84.4 | 84.4 | 98.7 | 98.7 |
| Example 23 | 100 | 2.4 | 2.4 | 80.2 | 80.2 | 82.6 | 82.6 |
| Example 24 | 100 | 8.5 | 8.5 | 87.7 | 87.7 | 96.2 | 96.2 |

As is noted from the results shown in Tables 1 and 2, in the case of using the cerium compound as the catalyst (Examples 1 to 24), it was perceived that the glycine is obtained in a high yield. In contrast, in the case of using zirconia as the catalyst under the equal conditions (Comparative Examples 1 to 7), the yield of glycine was very low as less than 2%.

In the case of using CeO$_2$ as the catalyst (Examples 1 to 10), when the reaction is performed for a longer time at a relatively low temperature, there was a tendency that the yield of glycine becomes higher.

In addition, in the case of using CeZrO$_4$ as the catalyst (Examples 11 to 19), it was perceived that the productivity of glycine is substantially equal to that in the case of using CeO$_2$.

In addition, in the case of using Li-supported CeO$_2$ as the catalyst (Examples 20 to 24), when ammonia is added (Examples 22 to 24), it was perceived that the yield of glycine is more improved.

The invention claimed is:

1. A method for producing glycine, comprising allowing glycinonitrile and water to react with each other in the presence of a cerium compound, to obtain glycine, wherein the cerium compound is a cerium-containing oxide which is a supported type metal oxide in which a component containing at least one metal element selected from the group consisting of lithium, iron, cobalt, nickel, copper, strontium, yttrium, indium, barium, lanthanum, praseodymium, neodymium, europium, lead, and hafnium is supported on a cerium oxide or a complex metal oxide of cerium and at least one other metal element, and wherein the method further comprises adding ammonia into the reaction system where glycinonitrile and water are allowed to react with each other in the presence of the cerium compound.

2. The method for producing glycine according to claim 1, wherein the other metal element in the complex metal oxide contains zirconium.

3. The method for producing glycine according to claim 1, wherein the metal element is selected from the group consisting of lithium, lanthanum, neodymium, yttrium, europium, and barium.

4. The method for producing glycine according to claim 1, wherein the metal element is lithium.

* * * * *